(12) United States Patent
Doak et al.

(10) Patent No.: US 9,289,787 B2
(45) Date of Patent: Mar. 22, 2016

(54) APPARATUS AND METHODS FOR A GAS DYNAMIC VIRTUAL NOZZLE

(71) Applicant: Arizona Board of Regents, a body corporate of the State of Arizona, Acting for and on behalf of Arizona State University, Scottsdale, AZ (US)

(72) Inventors: R. Bruce Doak, Tempe, AZ (US); John Spence, Tempe, AZ (US); Uwe Weierstall, Phoenix, AZ (US); Daniel P. DePonte, Hamburg (DE)

(73) Assignee: Arizona Board of Regents, A Body Corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 568 days.

(21) Appl. No.: 13/680,255

(22) Filed: Nov. 19, 2012

(65) Prior Publication Data

US 2013/0313336 A1    Nov. 28, 2013

Related U.S. Application Data

(63) Continuation of application No. PCT/US2011/038407, filed on May 27, 2011.

(60) Provisional application No. 61/349,206, filed on May 28, 2010.

(51) Int. Cl.
*B05B 17/00* (2006.01)
*A62C 5/02* (2006.01)
(Continued)

(52) U.S. Cl.
CPC .............. *B05B 7/0416* (2013.01); *B01L 3/0268* (2013.01); *B05B 1/00* (2013.01); *B05B 1/02* (2013.01);
(Continued)

(58) Field of Classification Search
CPC .......... B05B 7/0815; B05B 7/04; B05B 7/06; B05B 1/00; B05B 1/02; B05B 7/0416; H01J 49/165; B01L 3/0268; B01L 2200/12; B01L 2300/0838; G01N 23/2204
USPC ............ 239/8, 422, 423, 424, 428, 433, 589, 239/592, 593, 601
See application file for complete search history.

(56) References Cited

U.S. PATENT DOCUMENTS 3,314,611 A * 4/1967 McCartney ............... B05B 7/02
                                                            239/424
3,476,324 A * 11/1969 Kohnken ................. C03B 37/06
                                                            239/424
(Continued)

FOREIGN PATENT DOCUMENTS

EP          0647429         4/1995
WO       WO 99/30812       6/1999
(Continued)

OTHER PUBLICATIONS

Shapiro D.A et al, "Powder diffraction from a continuous microjet of submicrometer protein crystals", Journal of Synchrotron Radiation, vol. 15, pp. 593-599, 2008.
(Continued)

*Primary Examiner* — Steven J Ganey
(74) *Attorney, Agent, or Firm* — McDonnell Boehnen Hulbert & Berghoff LLP

(57) ABSTRACT

A nozzle for producing a liquid jet or a single-file stream of droplets of a fluid, methods using the nozzle, and an injector comprising the nozzle of the invention for providing the liquid jet or single-file stream of a fluid to a vacuum system are described.

28 Claims, 14 Drawing Sheets

(51) Int. Cl.
  *B05B 7/04* (2006.01)
  *H01J 49/16* (2006.01)
  *B05B 7/06* (2006.01)
  *B05B 7/08* (2006.01)
  *B05B 1/02* (2006.01)
  *B05B 1/00* (2006.01)
  *B01L 3/02* (2006.01)
  *G01N 23/22* (2006.01)

(52) U.S. Cl.
  CPC ... *B05B 7/04* (2013.01); *B05B 7/06* (2013.01); *B05B 7/0815* (2013.01); *G01N 23/2204* (2013.01); *H01J 49/165* (2013.01); *B01L 2200/12* (2013.01); *B01L 2300/0838* (2013.01)

(56) References Cited

U.S. PATENT DOCUMENTS

| | | | |
|---|---|---|---|
| 4,358,302 A | | 11/1982 | Dahneke |
| 4,514,160 A | * | 4/1985 | Davidsmeyer ...... B29C 45/2725 264/328.15 |
| 5,464,157 A | * | 11/1995 | Bourdoulous .......... B05B 7/045 239/424 |
| 5,848,751 A | | 12/1998 | Wang et al. |
| 6,386,463 B1 | | 5/2002 | Ganan-Calvo et al. |
| 6,478,240 B1 | | 11/2002 | Dorkin et al. |
| 6,554,202 B2 | | 4/2003 | Ganan-Calvo et al. |
| 7,201,335 B2 | * | 4/2007 | Babin ................. B29C 45/2711 239/589 |
| 8,272,576 B2 | | 9/2012 | Doak et al. |
| 2001/0010206 A1 | | 8/2001 | Bryning |
| 2009/0121038 A1 | * | 5/2009 | Wurz ................... B05B 7/0458 239/8 |

FOREIGN PATENT DOCUMENTS

| | | |
|---|---|---|
| WO | WO 99/30831 | 6/1999 |
| WO | WO 99/30832 | 6/1999 |
| WO | WO 99/30833 | 6/1999 |
| WO | WO 99/30834 | 6/1999 |
| WO | WO 99/30835 | 6/1999 |
| WO | WO 99/31019 | 6/1999 |
| WO | WO 01/45519 | 6/2001 |
| WO | WO 01/69289 | 9/2001 |
| WO | WO 00/76673 | 12/2001 |
| WO | WO 02/47744 | 6/2002 |
| WO | WO 02/060275 | 8/2002 |
| WO | WO 2005/018817 | 3/2005 |
| WO | WO 2006/117422 | 11/2006 |
| WO | WO 2009/091416 | 7/2009 |

OTHER PUBLICATIONS

Howells M et al, "An assessment of the resolution limitation due to radiation-damage in X-ray diffraction microscopy", Journal of Electron Spectroscopy and Related Phenomena, vol. 170, Issue 1-3, pp. 4-12, 2009.

Ganan-Calvo A.M et al, "Generation of steady liquid microthreads and micron-sized monodisperse sprays in gas", Physical Review Letters, vol. 80, Issue 2, pp. 285, 1998.

Deponte D.P. et al, "Gas dynamic virtual nozzle for generation of microscopic droplet streams", Journal of Physics D: Applied Physics, vol. 41, Issue 19, pp. 1-7, 2008.

Ganan-Calvo A et al, "Focusing capillary jets closet to the continuum limit", Nature Physics, vol. 3, Issue 10, pp. 737-742, 2007.

International Search Report for PCT/US2011/038407, mailed Sep. 15, 2011.

* cited by examiner

APPARATUS AND METHODS FOR A GAS DYNAMIC VIRTUAL NOZZLE

CROSS-REFERENCE TO RELATED APPLICATIONS

This application claims the benefit of the filing date of International Patent Application Serial No. PCT/US2011/038407, filed May 27, 2011, which in turn claims the benefit of U.S. Provisional Patent Application Ser. No. 61/349,206, filed May 28, 2010, which are hereby incorporated by reference in their entirety.

STATEMENT OF GOVERNMENT INTEREST

This invention was made with government support under Grant numbers 0919195 and 0555845 awarded by the National Science Foundation. The government has certain rights in the invention.

BACKGROUND OF THE INVENTION

Analysis and manipulation of particles, such as proteins or other biological molecules, often requires introducing or injecting the particle into vacuum, where the particle must maintain its native conformation. Examples of particle manipulation or analysis that may require particle injection into vacuum include molecular structure determination, spectroscopy, particle deposition onto a substrate (to produce, for example, sensor arrays), nanoscale free-form fabrication, formation of novel low temperature forms of particle-containing complexes, bombardment of particles by laser light, x-ray radiation, neutrons, or other energetic beams; controlling or promoting directed, free-space chemical reactions, possibly with nanoscale spatial resolution; and separating, analyzing, or purifying these particles.

Therefore, for many technological and scientific applications, the ability to form a single-file beam of microscopic liquid droplets is of great interest. Thus, methods and apparatus for providing streams of particles that are adapted for injection of the particle into vacuum would be of great benefit to these various fields.

SUMMARY OF THE INVENTION

In a first aspect, the invention provides a nozzle assembly comprising, (a) a housing, wherein a distal end of the housing defines an outlet channel, (b) a capillary tube disposed within the housing, wherein a distal end of the capillary tube is tapered, (c) at least one bore defined by the capillary tube, wherein the at least one bore defines a capillary outlet on a side surface of the tapered distal end, and (d) an asperity defined substantially on an apex of the tapered distal end.

In a second aspect, the invention provides a method for manufacturing a capillary tube, the method comprising: (a) heating the distal end of the capillary tube, (b) bending the distal end to a predetermined radius of curvature, (c) cutting the distal end at a desired distance along the radius of curvature, and (d) grinding a symmetrical cone onto the remaining portion of the distal end.

In a third aspect, the invention provides a method for manufacturing a capillary tube, the method comprising: (a) heating the distal end of the capillary tube until closure, (b) grinding the distal end into a cone, and (c) cutting at least one bevel into the cone.

In a fourth aspect, the invention provides a method for producing a liquid jet comprising (a) providing a nozzle assembly according to the first aspect of the invention, (b) injecting a first fluid into the proximal end of the housing, and (c) injecting a second fluid into the proximal end of the capillary tube. The nozzles described herein can produce a liquid jet whereby the second fluid exits the capillary outlet and flows along the surface of the tapered end to the asperity, and the first fluid acts upon the second fluid located on the asperity to create a liquid jet that flows through the outlet channel.

In a fifth aspect, the invention provides injectors comprising (i) a chamber comprising a vacuum orifice and an injector orifice, wherein the chamber is adapted for use with a vacuum analysis system; and (ii) a nozzle according to the preceding aspect, wherein the outlet channel of the nozzle outputs to the chamber and is essentially aligned with the injector orifice.

In a sixth aspect, the invention provides a nozzle assembly comprising, (a) a housing, wherein the housing defines a cavity enclosed on all sides with an inlet opening at a proximal end and a de Laval Nozzle at a distal end, wherein the de Laval Nozzle defines a converging-diverging channel, and wherein a housing outlet is defined within the de Laval Nozzle at the point where the converging-diverging channel is constricted, (b) a capillary tube disposed within the cavity of the housing such that there is a coaxial space maintained between the capillary tube and the housing, wherein a distal end of the capillary tube is optionally tapered, (c) at least one bore defined by the capillary tube, wherein a proximal end of the at least one bore defines a capillary inlet and a distal end of the at least one bore defines a capillary outlet, wherein the capillary outlet does not extend beyond the housing outlet, and (d) wherein the housing further defines a first propelling channel and a second propelling channel, wherein the first and second propelling channels are each disposed substantially perpendicular to the coaxial space and are in fluid communication with the coaxial space. In one embodiment of the sixth aspect, the invention further provides a first switching channel defined in the housing on a first side of a diverging section of the converging-diverging channel and a second switching channel defined in the housing on the second side of the diverging section of the converging-diverging channel, wherein the first and second switching channels are each in fluid communication with the diverging section of the converging-diverging channel.

In a seventh aspect, the invention provides a method for producing a liquid jet comprising (a) providing a nozzle assembly according to the sixth aspect of the invention, (b) injecting a first fluid into the first and the second propelling channels, and (c) injecting a second fluid into the capillary inlet. In one embodiment, the foregoing method further comprises operating at subsonic flow by maintaining an upstream-to-downstream pressure ratio in a converging-diverging channel in the range of about 1.03 to about 1.89. In another embodiment, the method further comprises (a) producing a liquid jet following a boundary layer of a first side of a diverging section of a converging-diverging channel, (b) injecting a first puff of air into a first switching channel, and (c) in response to the first puff of air, switching the liquid jet to a boundary layer of a second side of the diverging section of the converging-diverging channel. In an additional embodiment, the method further comprises (a) injecting a second puff of air into a second switching channel and (b) in response to the second puff of air, switching the liquid jet to the boundary layer of the first side of the diverging section of the converging-diverging channel. In still another embodiment, the method further comprises (a) operating the diverging section of the converging-diverging channel under vacuum and (b) in response to operating under vacuum, producing a liquid jet substantially centered between the first side and the second side of the diverging section of the converging-diverging channel.

In an eighth aspect, the invention provides a method for manufacturing the housing of the nozzle assembly of the sixth aspect, comprising, (a) soft-baking photoresist that is spin-coated in a desired pattern on a silicon wafer, (b) exposing the photoresist to UV light through a photomask, (c) chemically developing the photoresist, (d) hard-baking the photoresist to form a negative stamp, (e) pouring uncured poly(dimethylsiloxane) into the negative stamp to create a layer defining a cavity and a plurality of microchannels, and (f) fixing the layer between a top slab and a bottom slab of poly(methyl methacrylate).

DETAILED DESCRIPTION

Figure 1:
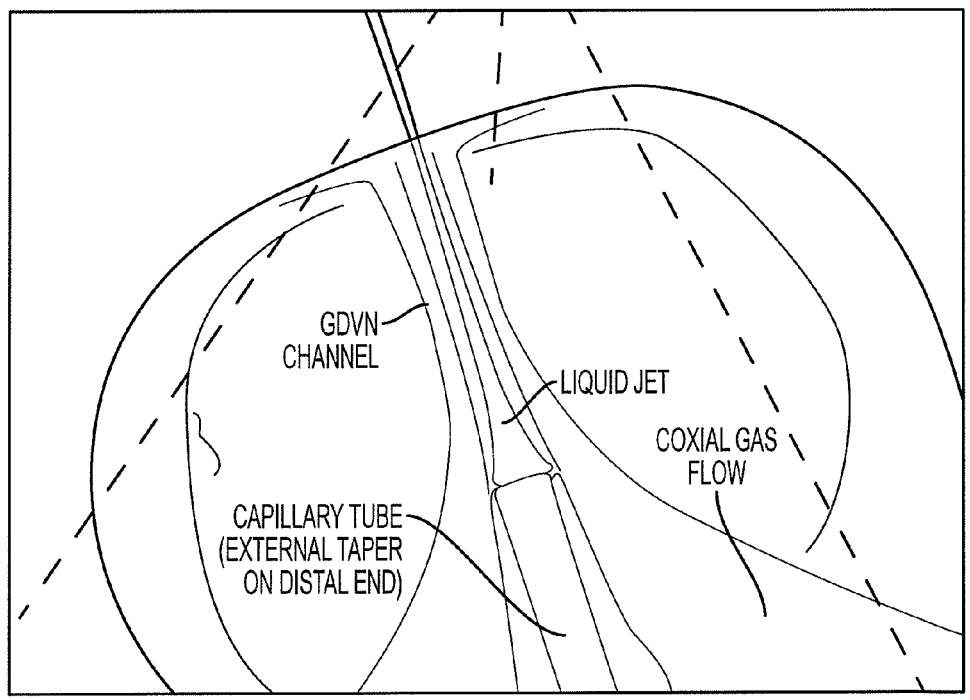
FIG. 1 is a cross-sectional view of a prior art nozzle.
Figure 2A:
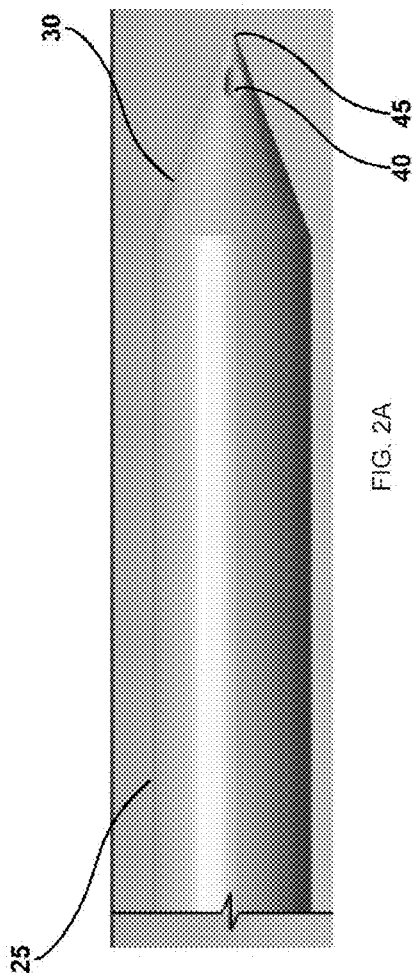
FIG. 2A is a side view of a capillary having a capillary outlet on a side surface of a tapered end.
Figure 2B:
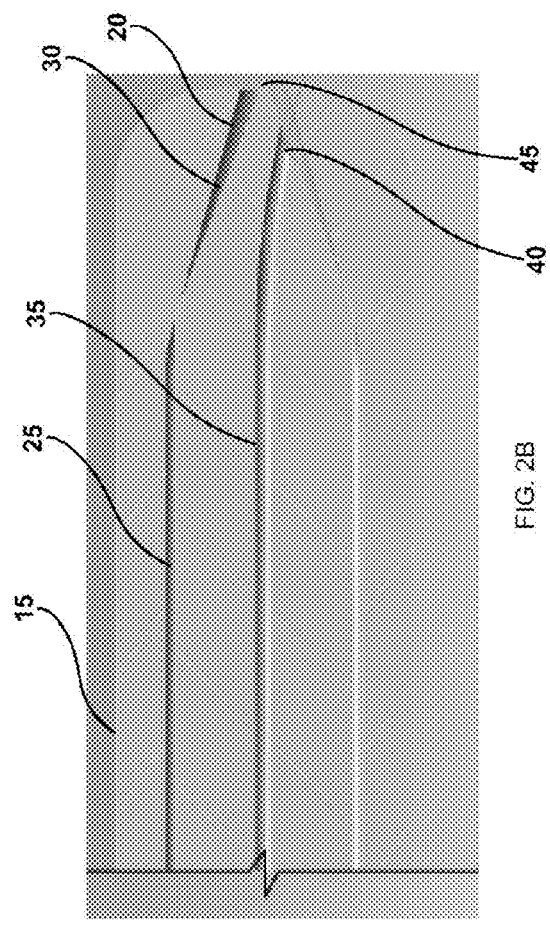
FIG. 2B is a cross-sectional side view of a nozzle assembly.
Figure 2C:
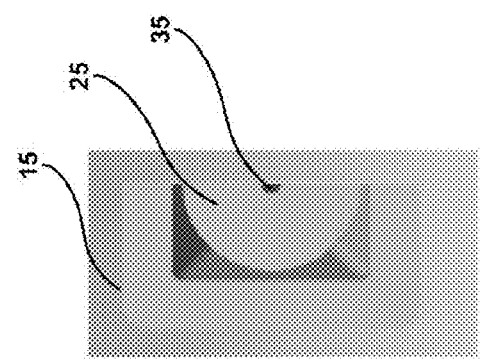
FIG. 2C is a cross-sectional end view of a nozzle assembly.

In a first aspect, as shown in FIGS. 2A-C, for example, a nozzle assembly comprises: (a) a housing 15, wherein a distal end of the housing defines an outlet channel 20, (b) a capillary tube 25 disposed within the housing 15, wherein a distal end of the capillary tube is tapered 30, (c) at least one bore 35 defined by the capillary tube 25, wherein the at least one bore 35 defines a capillary outlet 40 on a side surface of the tapered distal end, and (d) an asperity 45 defined substantially on an apex of the tapered distal end 30.

As used herein, the housing 15 is sized and shaped to receive the capillary tube 25. The housing's internal cross-section may take various forms, for example, circular, square, triangular hexagonal, etc., essentially any symmetric cross-section that allows ample access for a first fluid, preferably a gas, to have a sufficient gas flow rate and symmetrical gas flow pattern. Note that asymmetry in gas flow can force the resulting filamentary liquid jet to emerge from the outlet channel off-axis. In one embodiment, the housing's internal cross-section is circular, and the inner diameter of the housing 15 is greater than the outer diameter of the capillary tube 25 such that there is a coaxial space between the housing's inner wall and the capillary tube's external wall. In another embodiment, the housing 15 defines a square internal cross-section, as shown in FIGS. 2B-C, such that the four corners of the housing provide sufficient access for gas flow.

The distal end of the housing may be formed into a symmetric convergent taper to create the outlet channel 20. Alternatively, the outlet channel 20 may have a constant diameter along its length. As used herein, the outlet channel 20 is a constricting aperture that receives both gas flow and a liquid stream emerging from the capillary tube 25. The capillary tube 25 is preferably substantially aligned along the axis of the outlet channel 20.

Figure 5A:
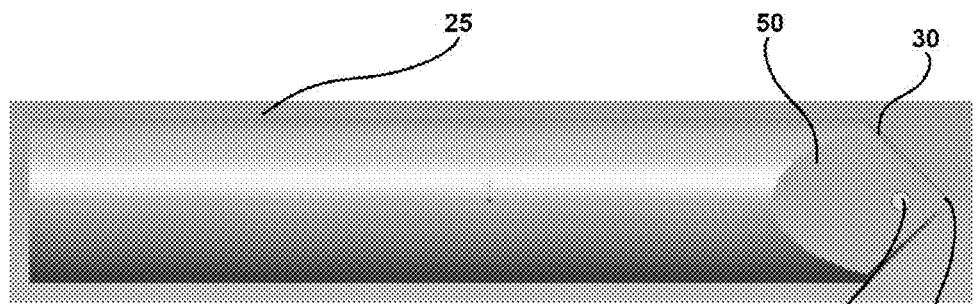
FIG. 5A is a side view of a capillary tube with a coned and beveled distal end.
Figure 5B:
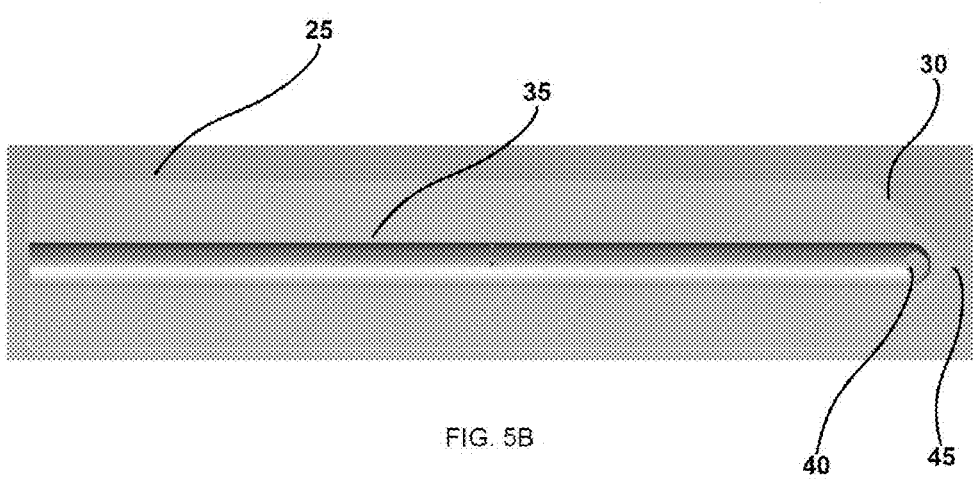
FIG. 5B is a cross-sectional side view of a capillary tube with a coned and beveled distal end.
Figure 5C:
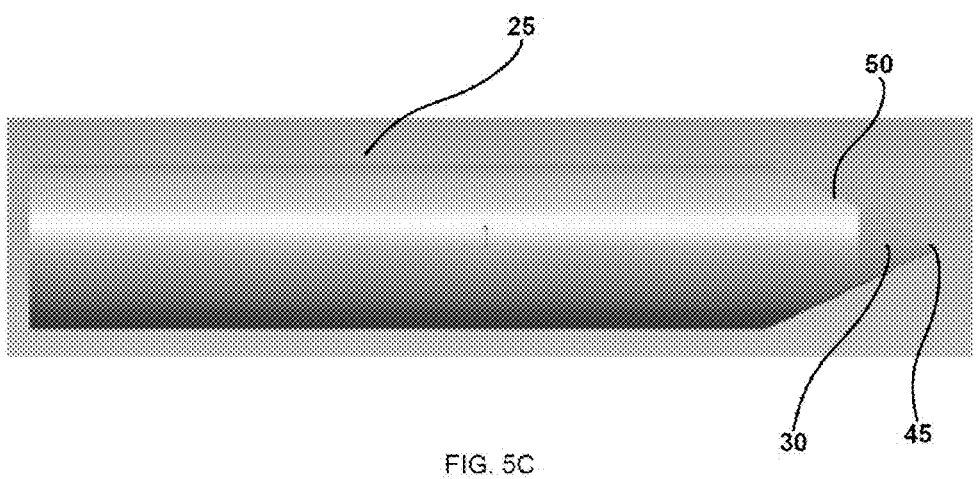
FIG. 5C is a top view of a capillary tube with a coned and beveled distal end.

As used herein, the capillary tube 25 has at least one bore 35 through which a second fluid flows. In one embodiment, the capillary tube's tapered end 30 is received in the outlet channel 20. In order to aid in self-centering alignment of the capillary tube 25 within the housing 15, the capillary tube's tapered end 30 may be substantially conical. Alternatively, as shown in FIGS. 5A-C, the capillary tube's tapered end 30 may be substantially conical and beveled. This has the advantage of providing two different angles to facilitate adaptability of insertion of the capillary tube 25 into the outlet channel 20. This embodiment may operate with a single bevel as well.

In yet another embodiment, the capillary tube's tapered end 30 defines a plurality of planar flats (not shown), preferably with a minimum of at least three planar flats to achieve adequate gas flow. In certain embodiments, three to about ten planar flats are provided on the capillary tube's tapered end 30. In certain embodiments, three to about eight planar flats; or three to about six planar flats are provided on the capillary tube's tapered end 30. In certain embodiments, three flats; or four flats; or five flats, or six flats; or seven flats; or eight flats; or nine flats; or ten flats are provided on the capillary tube's tapered end 30.

These planar flats take the form of symmetric apertures evenly spaced and equally angled about the periphery of the tapered end 30 of the capillary tube 25 through which the gas flow can merge between the tapered end 30 and housing 15, when the tapered end 30 and outlet channel 20 are mated together to achieve self-centering. In alternative embodiments, the capillary tube's tapered end 30 is positioned upstream of or even with the outlet channel 20.

This self-centering methodology results in the liquid jet being injected directly into a supersonic free jet expansion of the gas, as opposed to injection into the convergent continuum gas flow just upstream of the nozzle. That a linear filamentary liquid jet can be generated in this fashion was unexpected.

Figure 6A:
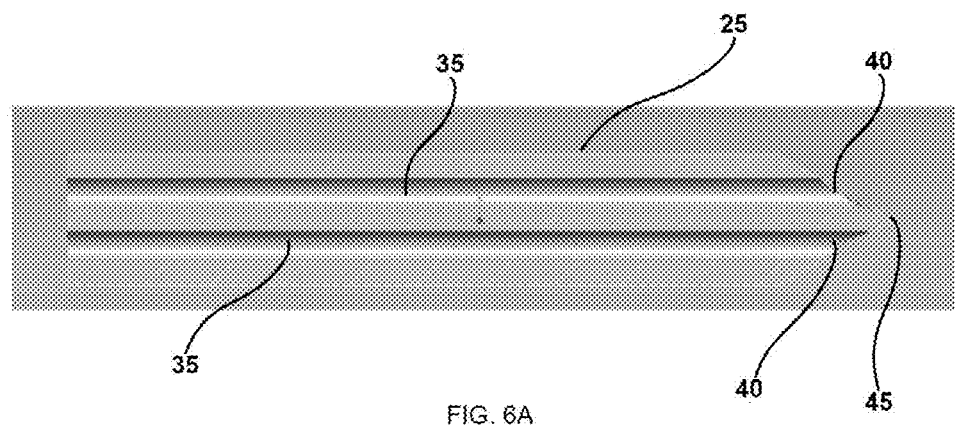
FIG. 6A is a cross-sectional side view of a double-bore straight capillary tube with a distal end in the shape of a cone.
Figure 6B:
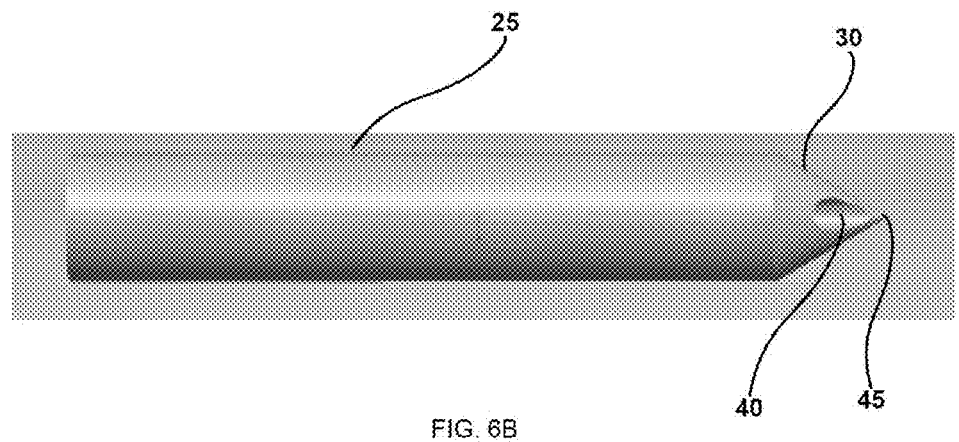
FIG. 6B is a top view of a double-bore straight capillary tube with a distal end in the shape of a cone.

As used herein, the at least one bore 35 extends along the length of the capillary tube 25 to the distal end 30. In one embodiment, as shown in FIGS. 2A-C, 3A-B, 4A-C, 5A-C, the at least one bore 35 comprises a single bore 35 that is aligned with the central axis of the capillary tube 25. This single bore 35 may diverge from the capillary tube's central axis to define the capillary outlet 40 on a side surface of the tapered end (FIGS. 2A-C, 3A-B, 4A-C). Alternatively, at least one bevel 50 is cut into a closed distal end 30 of the capillary tube 25 to reveal the single bore 35 resulting in a capillary outlet 40 on a side surface of the capillary tube's distal end 30. In yet another embodiment, as shown in FIGS. 6A-B, the at least one bore 35 is parallel to but spaced apart from the central axis of the capillary tube 25. In the case where the capillary tube 25 defines two (or more) bores 35, the second fluid could flow through either or both of the bores 35. Alternatively, two reacting liquids could be sent separately down the respective bores 35 to be mixed at the tip of the capillary tube's distal end 30.

As used herein, an asperity 45 is a slight projection (e.g., a point or bump) from the exterior surface of the capillary tube 25. The asperity 45 is preferably centered on the distal end 30 of the capillary tube 25, such that the asperity 45 is automatically centered when the capillary tube 25 is inserted in the housing 15. The provision of an asperity 45 has the advantageous effect of controlling the point at which the second fluid will emerge from the capillary tube 25, since the liquid jet will emerge from the most pronounced asperity 45 present on the distal end 30 of the capillary tube 25.

Figure 3A:
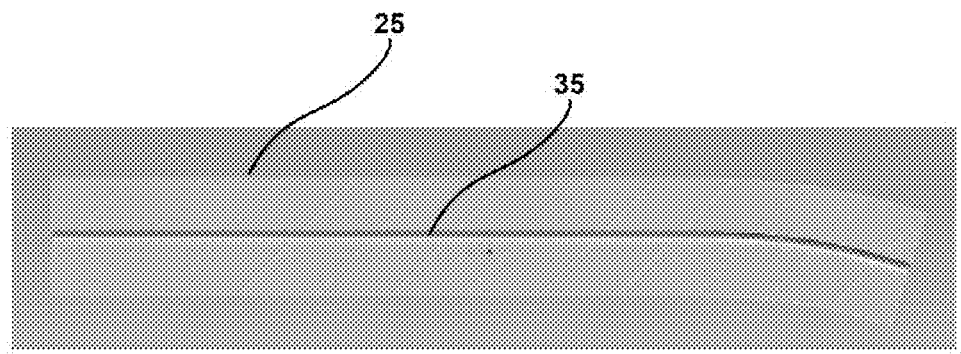
FIG. 3A is a cross-sectional side view of a capillary tube with the distal end bent to a predetermined radius of curvature.
Figure 3B:
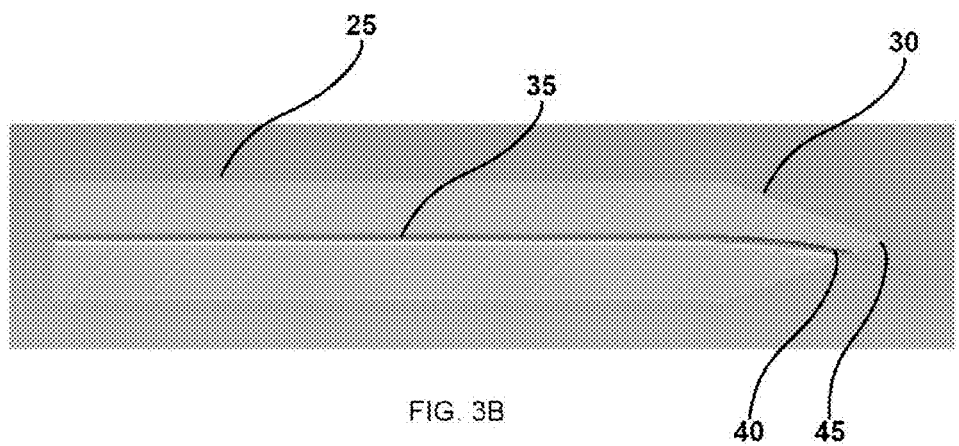
FIG. 3B is a cross-sectional side view of a capillary tube with the distal end cut and ground into a symmetrical cone.

In a second aspect, as shown in FIGS. 3A-B, the invention provides a method for manufacturing a capillary tube 25, the method comprising: (a) heating the distal end 30 of the capillary tube 25, (b) bending the distal end 30 to a predetermined radius of curvature, (c) cutting the distal end 30 at a desired distance along the radius of curvature, and (d) grinding a symmetrical cone onto the remaining portion of the distal end 30.

In certain embodiments, the capillary can be rotated during the grinding or heating or both to symmetrize any gravitational forces during heating, to provide highly axisymmetric capillary tip geometries.

Figure 4A:
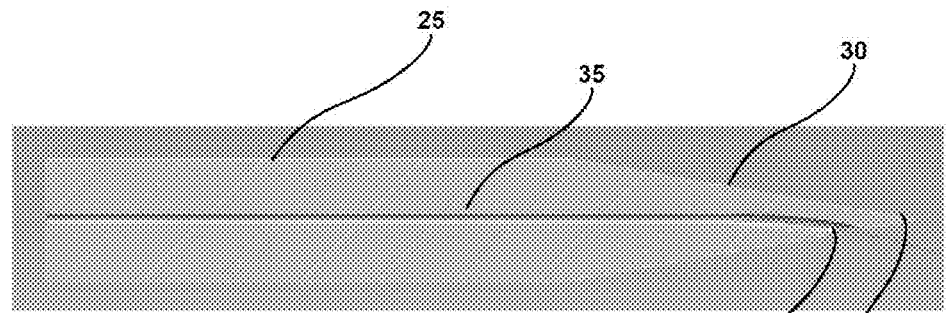
FIG. 4A is a cross-sectional side view of an embodiment of a capillary tube's distal end geometry.
Figure 4B:
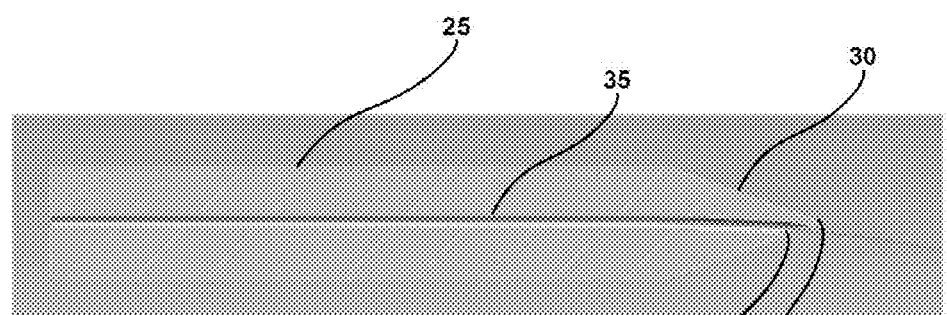
FIG. 4B is a cross-sectional side view of an embodiment of a capillary tube's distal end geometry.
Figure 4C:
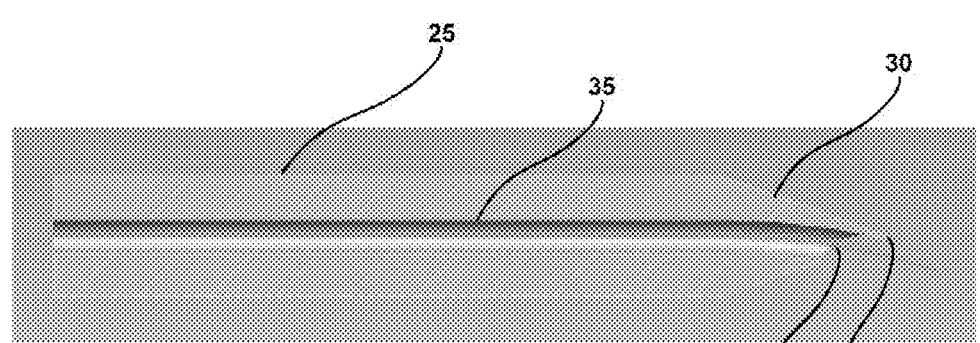
FIG. 4C is a cross-sectional side view of an embodiment of a capillary tube's distal end geometry.

The position of the capillary outlet 40 is determined by cone angle, the predetermined radius of curvature, and the position of the cut within the radius of curvature. Examples of different positions for the capillary outlet 40 are illustrated in FIGS. 4A-C. This method of manufacturing is preferably employed with a capillary tube 25 defining a single central bore 35.

In a third aspect, as shown in FIGS. 5A-C, the invention provides a method for manufacturing a capillary tube 25, the method comprising: (a) heating the distal end 30 of the capillary tube 25 until closure, (b) grinding the distal end 30 into a cone, and (c) cutting at least one bevel 50 into the cone. The face of each bevel 50 will define a capillary outlet 40.

Figure 7:
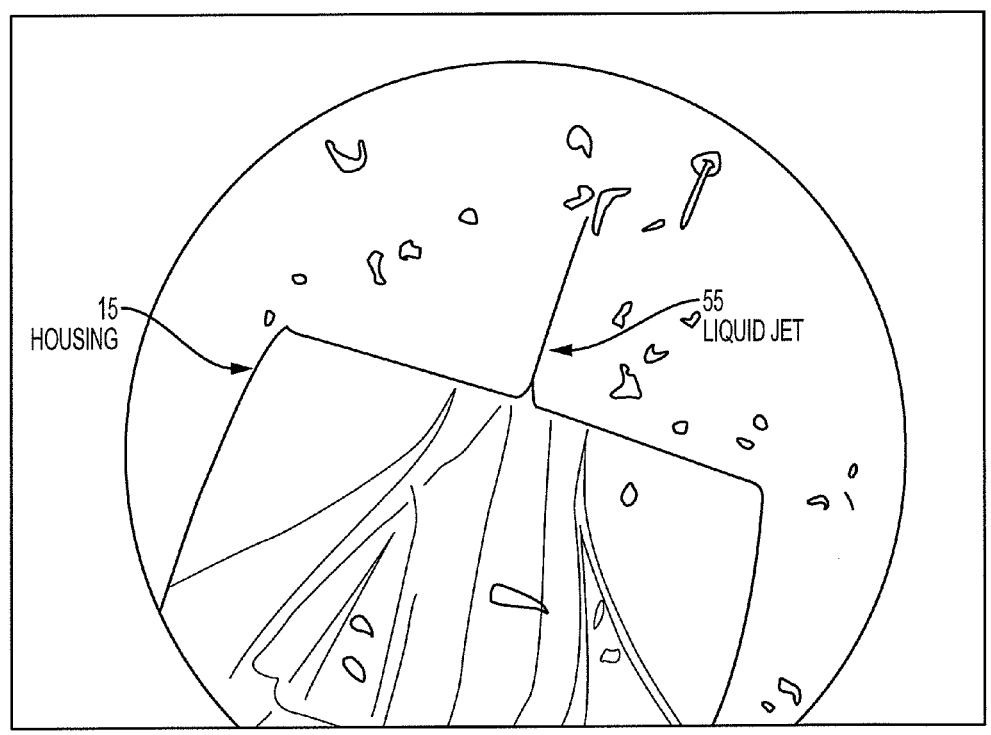
FIG. 7 is a side view of the nozzle assembly generating an asperity-guided liquid jet at the tip of the distal end of a coned capillary tube.

In a fourth aspect, as shown in FIG. 7, the invention provides a method for producing a liquid jet 55 comprising (a) providing a nozzle assembly 10 according to the first aspect of the invention, (b) injecting a first fluid into the proximal end of the housing 15, (c) injecting a second fluid into the proximal end of the capillary tube 25, (d) the second fluid exiting the capillary outlet 40 at the tapered end 30 which contains an asperity 45 on its periphery, and (e) the first fluid acting upon the second fluid to create a liquid jet 55 that emerges from the asperity 45 and flows through the outlet channel 20.

As used herein, the first fluid is preferably a gas. For example, in some embodiments, the first fluid comprises one or more inert gases flowing through the housing. The term "inert gas" as used herein means a gas which will not cause degradation or reaction of the fluids and/or any analytes. Such gases preferably contain limited levels of oxygen and/or water; however, the acceptable level of water and/or oxygen will depend on the fluids and/or analytes, and is readily apparent to one skilled in the art. Such atmospheres preferably include gases such as, but are not limited to, hydrogen, nitrogen, carbon dioxide, helium, neon, argon, krypton, xenon, volatile hydrocarbon gases, or mixtures thereof. In certain embodiments, the inert gas comprises nitrogen, helium, argon, or a mixture thereof. In certain embodiments, the inert gas comprises nitrogen. In certain embodiments, the inert gas comprises helium. In certain embodiments, the inert gas comprises argon.

When the first fluid is a gas, it is preferably supplied to the housing at pressures ranging from about 2 to 200 times atmospheric, or about 2 to 100 times atmospheric pressure; or about 2 to 50 times atmospheric pressure; or about 2 to 25 times atmospheric pressure; or about 2 to 15 times atmospheric pressure; or about 2 to 10 times atmospheric pressure; more preferably, at pressures ranging from about 2 to 5 times atmospheric pressure; or pressures ranging from about 3 to 5 times atmospheric pressure; or pressures ranging from about 5 to 200 times atmospheric pressure, or 5 to 100 times atmospheric pressure; or about 5 to 50 times atmospheric pressure; or about 5 to 25 times atmospheric pressure; or about 5 to 15 times atmospheric pressure; or about 5 to 10 times atmospheric pressure; or pressures ranging from about 9 to 200 times atmospheric pressure, or about 9 to 100 times atmospheric pressure; or about 9 to 50 times atmospheric pressure; or about 9 to 25 times atmospheric pressure; or about 9 to 15 times atmospheric pressure.

As used here, the second fluid is preferably a liquid. In some embodiments the second fluid further comprises an analyte; such second fluids preferably comprise a heterogeneous or homogeneous solution, or particulate suspension of the analyte in the second fluid. The second fluid includes, but is not limited to, water and various solutions of water containing detergents, buffering agents, anticoagulants, cryoprotectants, and/or other additives as needed to form analyte-containing jets or droplets while maintaining the analyte in a desired molecular conformation. Preferred analytes include, but are not limited to, proteins, protein complexes, peptides, nucleic acids (e.g., DNAs, RNAs, mRNAs), lipids, functionalized nanoparticles, viruses, bacteria, and whole cells.

When the second fluid comprises a liquid, it is preferably supplied to the capillary tube at pressures ranging from about 2 to 35 times atmospheric pressure; more preferably, at pressures ranging from about 10 to 20 times atmospheric pressure; or pressures ranging from about 15 to 20 times atmospheric pressure.

In certain embodiments, the first fluid comprises a gas and the second comprises a liquid.

In operation, as shown in FIG. 2 and FIG. 7, the first fluid exerts gas dynamic forces on the liquid stream emerging from the capillary tube 25, significantly reducing the diameter of the liquid stream. The liquid stream preferably emerges from the constriction as a contiguous, linear, filamentary liquid jet 55 of microscopic diameter. Liquid jet 55 can be much smaller than the capillary bore 35 from which it emerges. The liquid jet 55 may take the form of a single-file stream of droplets.

For example, the liquid jet 55 can have a diameter between about 1 μm and 100 nm. In certain embodiments, the liquid jet can have a diameter between about 900 nm and 100 nm; or about 800 nm and 100 nm; or about 700 nm and 100 nm; or about 600 nm and 100 nm; or about 500 nm and 100 nm.

In a fifth aspect, the invention provides injectors comprising (i) a chamber comprising a vacuum orifice and an injector orifice, wherein the chamber is adapted for use with a vacuum analysis system; and (ii) a nozzle as described above, wherein the outlet channel of the nozzle outputs to the chamber and is essentially aligned with the injector orifice.

The term "essentially aligned" as used herein with respect to two orifices means that the vector at the center of a first orifice and normal to the plane defined by the first orifice intersects and is essentially normal (e.g., 90°+/−10°, preferably +/−5°) to the plane defined by the second orifice, and intersects the plane defined by the second orifice within the boundary of the second orifice. More preferably, the vector at the center of a first orifice and normal to the plane defined by the first orifice is essentially normal to the plane defined by the second orifice and intersects the plane defined by the second orifice essentially at the center (e.g., within 10% of the total diameter of the orifice; preferably, within 5%) of the second orifice.

In operating the injector of the invention, a vacuum is maintained in the chamber via the vacuum orifice and a liquid jet is provided by the nozzle as discussed previously. Preferably, the vacuum in the injector is maintained at a level less than or equal to the vacuum maintained within the vacuum analysis system.

The injector allows for the liquid jet to be injected into a vacuum analysis system. Such systems may involve samples analyzed under pressures ranging from ultra-high vacuum (UHV) or high vacuum (HV) up to one atmosphere (e.g., environmental scanning electron microscopy (e-SEM) or environmental tunneling electron microscopy (e-TEM)). For example, the samples may be analyzed under pressures ranging from about 100 torr to about $10^{-9}$ mbar. In certain embodiments, the samples are analyzed under pressures suitable for environmental imaging methods, such as, but not limited to, pressures ranging from about 0.1 torr to 100 torr; or 0.1 torr to 10 torr, or 0.1 mbar to 1 torr.

In an embodiment of the invention, the injector of the invention further comprises a vacuum pump for providing a vacuum in the first chamber via the vacuum orifice.

In a preferred embodiment, the injector orifice comprises a simple aperture. In another preferred embodiment of the third aspect, the injector orifice comprises a tube. In a more preferred embodiment of the third aspect, the injector orifice further comprises a molecular beam skimmer.

The injector of the invention may further comprise an aligner for aligning the outlet channel of the nozzle with the injector orifice. Such aligners include mechanical alignment, such as via thumbscrews, or mechano-piezoelectric devices, such as precision mechanical drives or precision piezoelectric drives that move the capillary laterally and axially with respect to the injector orifice. The aligner may be sealed within the assembly which comprises the injector of the invention and/or pass through vacuum seals, so that the only physical communication between the nozzle and the surrounding plenum is via the nozzle exit orifice and the only physical communication between the plenum and the surrounding ambient is via the injector orifice.

In a sixth aspect, shown in FIGS. 10-13, for example, the invention provides a nozzle assembly comprising, (a) a housing 100, wherein the housing 100 defines a cavity enclosed on all sides with an inlet opening 105 at a proximal end and a de Laval Nozzle 110 at a distal end, wherein the de Laval Nozzle 110 defines a converging-diverging channel, and wherein a housing outlet 115 is defined within the de Laval Nozzle 110 at the point where the converging-diverging channel is constricted, (b) a capillary tube 120 disposed within the cavity of the housing such that there is a coaxial space 125 maintained between a portion of the capillary tube 120 and a portion of the housing 100, wherein a distal end 130 of the capillary tube 120 is optionally tapered, (c) at least one bore 135 defined by the capillary tube 120, wherein a proximal end of the at least one bore defines a capillary inlet 140 and a distal end of the at least one bore defines a capillary outlet 145, wherein the capillary outlet 145 does not extend beyond the housing outlet 115, and (d) wherein the housing 100 further defines a first propelling channel 150 and a second propelling channel 155, wherein the first and the second propelling channels 150, 155 are each disposed substantially perpendicular to the coaxial space 125 and are in fluid communication with the coaxial space 125.

As used herein, a "de Laval Nozzle" means a convergent-divergent channel in the shape of an asymmetric hourglass. The de Laval Nozzle is used to accelerate first and second fluids passing through the constriction defining the housing outlet 115, where the nozzle transitions from converging to diverging. Thus, in a preferred embodiment, the capillary outlet 145 remains proximal of the housing outlet 115 to obtain the maximum benefits of the acceleration of fluid through the nozzle constriction. In one embodiment, the housing outlet 115 has a rectangular cross-section, shown in FIG. 11.

As used herein, a "coaxial space" means that a substantially uniform separation is maintained between a portion of the housing and a portion of the outer surface of the capillary tube.

Figure 10:
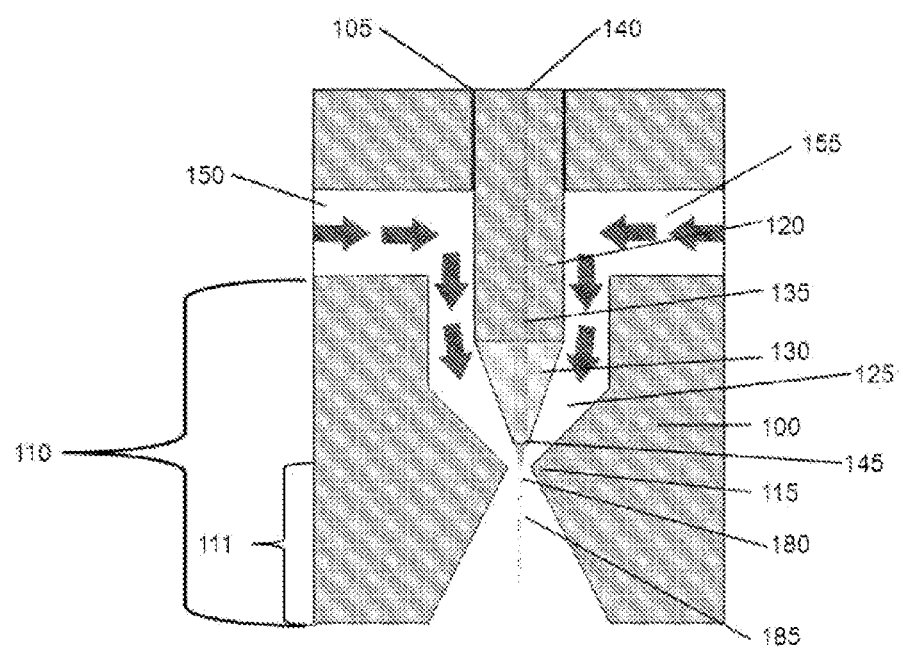
FIG. 10 is a top cross-sectional view of the nozzle assembly producing a liquid jet and droplet stream according to the sixth aspect of the invention.

In one embodiment of the sixth aspect, the first propelling channel 150 and the second propelling channel 155 are disposed on opposing sides of the housing 100, as shown in FIG. 10. A fluid is injected into the first and the second propelling channels 150, 155, flows into the coaxial space 125 and then out through the housing outlet 115 into the divergent section 111 of the converging-diverging channel 110. As such, one benefit of arranging the first and second propelling channels 150, 155 on opposing sides of the housing 100 is even fluid distribution within the coaxial space 125.

Figure 13:
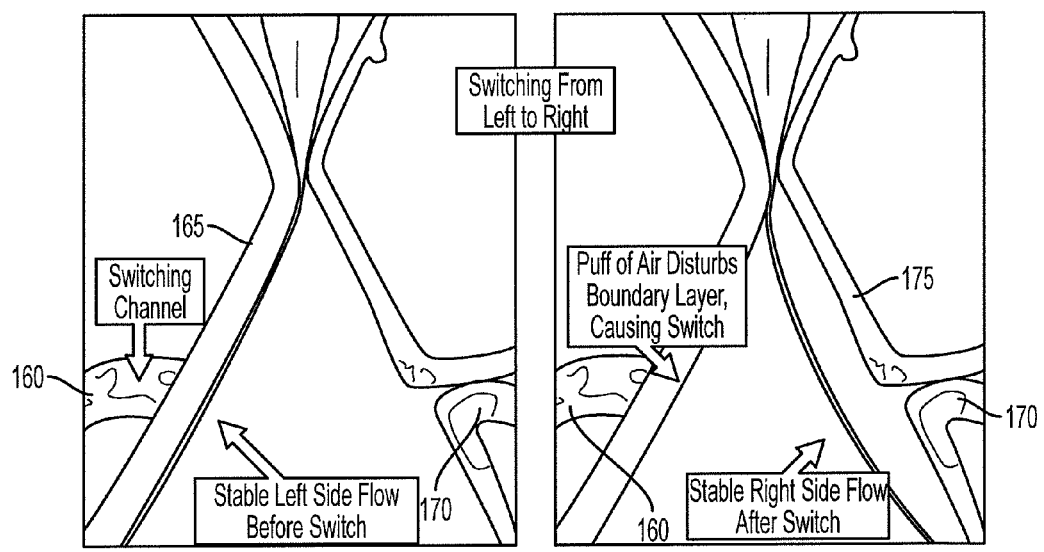
FIG. 13 shows two images each of a detail view of the distal end of the nozzle assembly according to the sixth aspect of the invention producing a liquid jet following a boundary layer of a first side of a diverging section of a converging-diverging channel and a liquid jet following a boundary layer of a second side of a diverging section of a converging-diverging channel, as well as first and second switching channels.

In one embodiment of the sixth aspect, shown in FIG. 13, the invention further provides a first switching channel 160 defined in the housing 100 on a first side 165 of a diverging section 111 of the converging-diverging channel 110 and a second switching channel 170 defined in the housing 100 on the second side 175 of the diverging section 111 of the converging-diverging channel 110, wherein the first and second switching channels 160, 170 are each in fluid communication with the diverging section 111 of the converging-diverging channel 110. As explained below, in operation, when the liquid jet 180 is flowing along the boundary layer 165 of the side of the diverging section in which a switching channel 160 is disposed, that switching channel 160 directs a discrete puff of air into the liquid jet 180. The puff of air disturbs the boundary layer and causes the liquid jet 180 to switch to the boundary layer 175 on the opposite side of the diverging section 111. The liquid jet 180 can then be sent back to the original boundary layer 160 through a second discrete puff of air directed through the other switching channel 170, which is now adjacent the liquid jet 180. The ability to switch the flow from one boundary layer to the other provides a way to conserve the fluids by delivering the liquid jet 180 only during an X-ray pulse, discussed in more detail below.

In a seventh aspect, the invention provides a method for producing a liquid jet 180 comprising (a) providing a nozzle assembly according to the sixth aspect of the invention, (b) injecting a first fluid into the first and second channels 150, 155, and (c) injecting a second fluid into the capillary inlet 140. In one embodiment, the first fluid is helium gas.

As discussed above, a "liquid jet" ranges from a substantially constant stream of fluid 180 to a single-file stream of droplets 185.

In one embodiment, the foregoing method further comprises operating at subsonic flow by maintaining an upstream-to-downstream pressure ratio in a converging-diverging channel 110 in the range of about 1.03 to about 1.89. As used herein, "upstream" refers to the pressure maintained in the converging section of the de Laval Nozzle 110 and "downstream" refers to the pressure maintained in the diverging section 111 of the de Laval Nozzle 110. The pressure in the converging section and diverging sections can be calculated based on the geometry of the de Laval Nozzle 110 and the pressure at which liquid is injected into the first and second propelling channels 150, 155.

Figure 12:
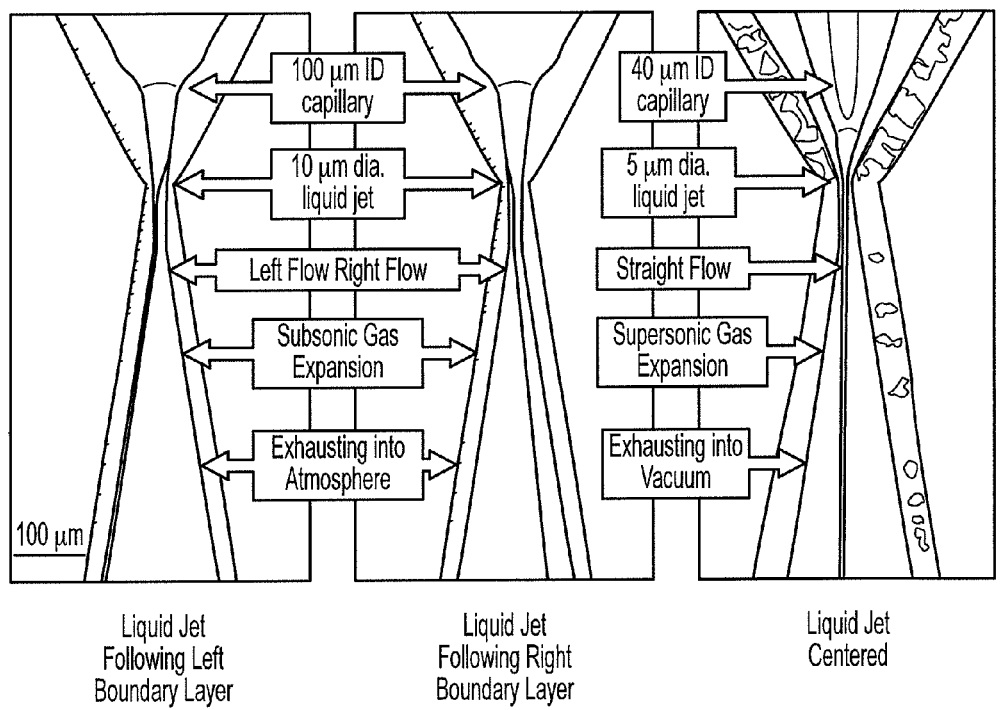
FIG. 12 shows three images each of a detail view of the distal end of the nozzle assembly according to the sixth aspect of the invention producing a liquid jet following a boundary layer of a first side of a diverging section of a converging-diverging channel, a liquid jet following a boundary layer of a second side of a diverging section of a converging-diverging channel, and a liquid jet substantially centered between the first side and the second side of the diverging section of the converging-diverging channel.

In another embodiment, shown in FIG. 12, the method further comprises (a) producing a liquid jet 180, 185 following a boundary layer of a first side 165 of a diverging section of a converging-diverging channel 110, (b) injecting a first puff of air into a first switching channel 160, and (c) in response to the first puff of air, switching the liquid jet 180, 185 to a boundary layer of a second side 175 of the diverging section 111 of the converging-diverging channel 110. In an additional embodiment, shown in FIG. 12, the method further comprises (a) injecting a second puff of air into a second switching channel 170 and (b) in response to the second puff of air, switching the liquid jet 180, 185 to the boundary layer of the first side 165 of the diverging section 111 of the converging-diverging channel 110. Both of the foregoing embodiments are achieved when the diverging section 111 of the converging-diverging channel 110 is maintained at atmospheric pressure.

In still another embodiment, shown in FIG. 12, the method further comprises (a) operating the diverging section 111 of the converging-diverging channel 110 under vacuum and (b) in response to operating under vacuum, producing a liquid jet 180, 185 substantially centered between the first side 165 and the second side 175 of the diverging section 111 of the converging-diverging channel 110.

In an additional embodiment, the method further comprises directing the liquid jet 180 across a pulsed X-ray beam. Here, a very powerful X-ray source, such as the Linac Coherent Light Source, for example, is utilized with a femtosecond pulse duration while a liquid jet 180 under vacuum is directed across the path of the X-ray, to conduct experiments capturing results utilizing crystallography.

Figure 11:
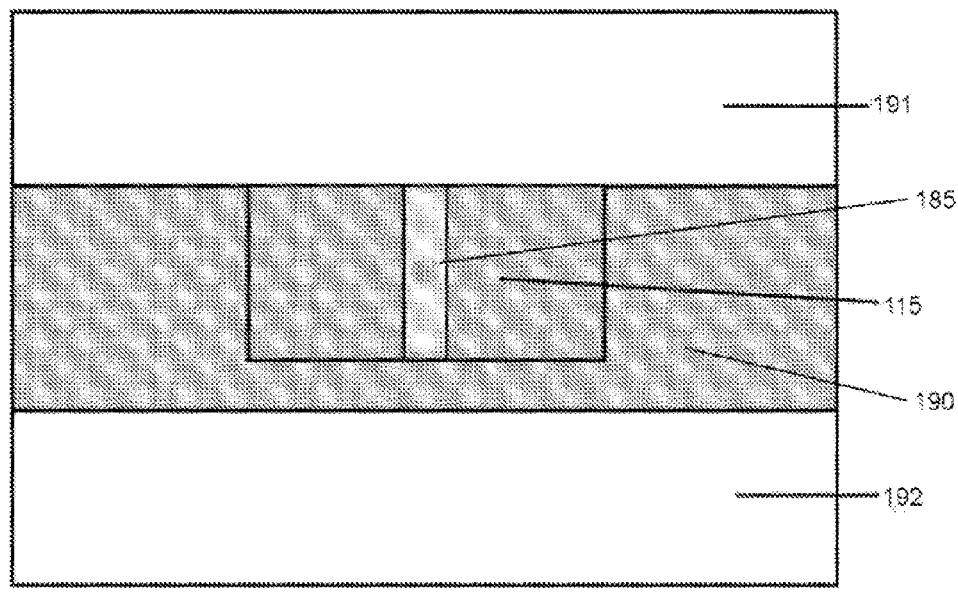
FIG. 11 is an end view of the nozzle assembly producing a liquid jet and droplet stream according to the sixth aspect of the invention.

In an eighth aspect, the invention provides a method for manufacturing the housing of the nozzle assembly of the sixth aspect, comprising, (a) soft-baking photoresist that is spin-coated in a desired pattern on a silicon wafer, (b) exposing the photoresist to UV light through a photomask, (c) chemically developing the photoresist, (d) hard-baking the photoresist to form a negative stamp, (e) pouring uncured poly(dimethylsiloxane) into the negative stamp to create a layer 190 defining a cavity and a plurality of microchannels, and (f) fixing the layer between a top slab 191 and a bottom slab 192 of poly (methyl methacrylate), as shown for example in FIG. 11.

EXAMPLES

Example 1

Preparation of a Nozzle

Figure 8A:
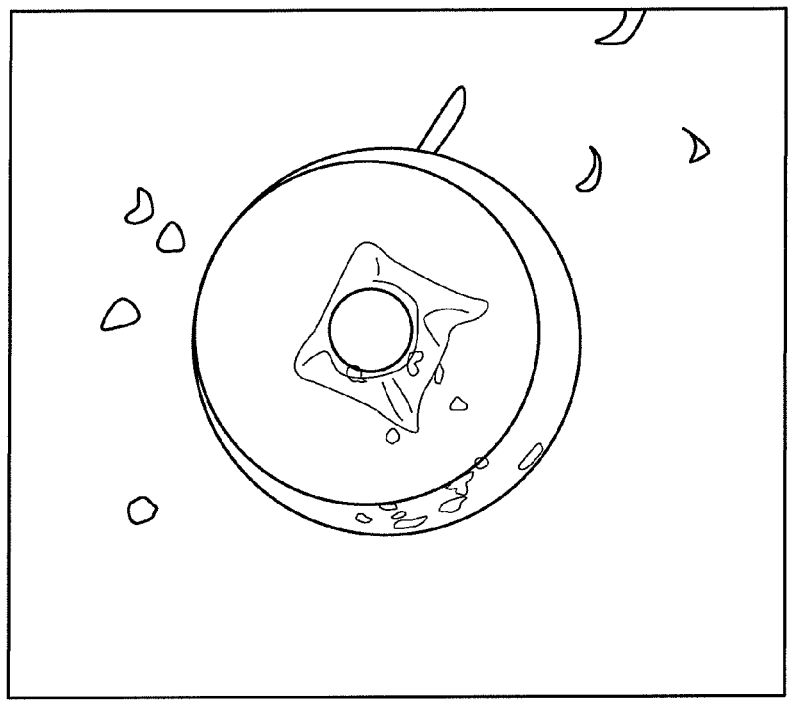
FIG. 8A shows a pyramidal exit channel that tapers continuously from the square tube cross section to a quadra-oval aperture of approximately 100 micrometer diameter in a flat distal end.
Figure 8B:
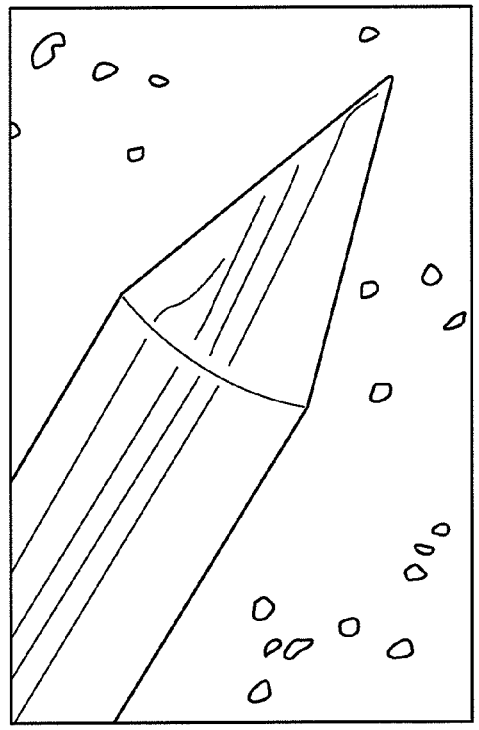
FIG. 8B is an image showing the bore of the capillary exiting through a conical taper at a chosen distance back from the conical tip.
Figure 8C:
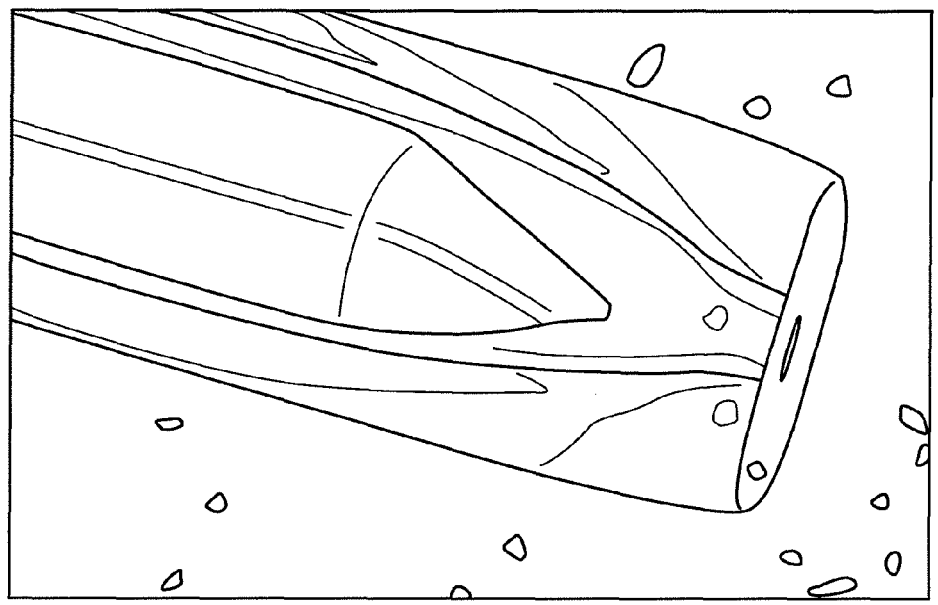
FIGS. 8C and 8D are images showing that the capillary cone surface comes into contact with the flat internal pyramidal sides of the outer housing in the exemplary embodiment described in Example 1.
Figure 8D:
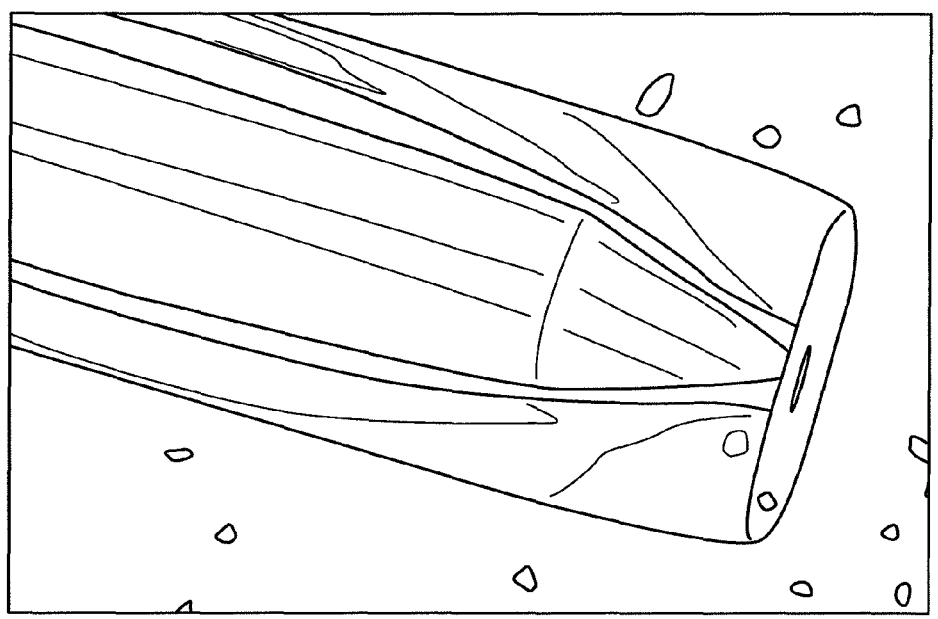

One example for fabricating an asperity-guided GDVN injector nozzle is as follows: The outer housing of the injector assembly is fabricated from a short section, e.g., 1 inch long, of glass tube having square cross section with inner wall-to-wall spacing of 400 micrometer. One end of this square tube is flame polished and ground back perpendicularly to the tube axis to obtain a pyramidal exit channel that tapers continuously from the square tube cross section to a quadra-oval aperture of approximately 100 micrometer diameter in a flat distal end as shown in FIG. 8A. An inner capillary having a central asperity is formed by briefly heating then bending the end of a long silica capillary, e.g. 50 inches, of 360 micrometer OD and 50 micrometer ID as in FIG. 3A. The capillary is then placed in a custom grinding apparatus that rotates the capillary about its axis as its bent end is brought into contact under microscope control with the moving abrasive surface of a commercial polishing machine. The angle of contact and the position of contact relative to the bend are adjusted such that a conical taper of 15 degrees cone half-angle is cut onto the end of the capillary, with the bore of the capillary exiting through this conical taper at a chosen distance back from the conical tip as in FIGS. 3B and 8B. This tapered end of the capillary is inserted through the proximal end of the square glass tube such that the capillary cone surface comes into contact with the flat internal pyramidal sides of the outer housing as in FIGS. 8C and 8D, thereby centering the conical end of the capillary relative to the pyramidal channel. The quadra-oval shape of the pyramidal channel provides four highly symmetrical gaps between the outer housing and the inner conical cone, with the tip of the cone providing a centered asperity on the axis of the assembly. A second capillary to supply the coaxial fluid flow is then inserted a short distance into the proximal end of the square tube, parallel to the tapered capillary, and the two capillaries glued into place.

Example 2

Application to Environmental Transmission Electron Microscopy

Figure 9:
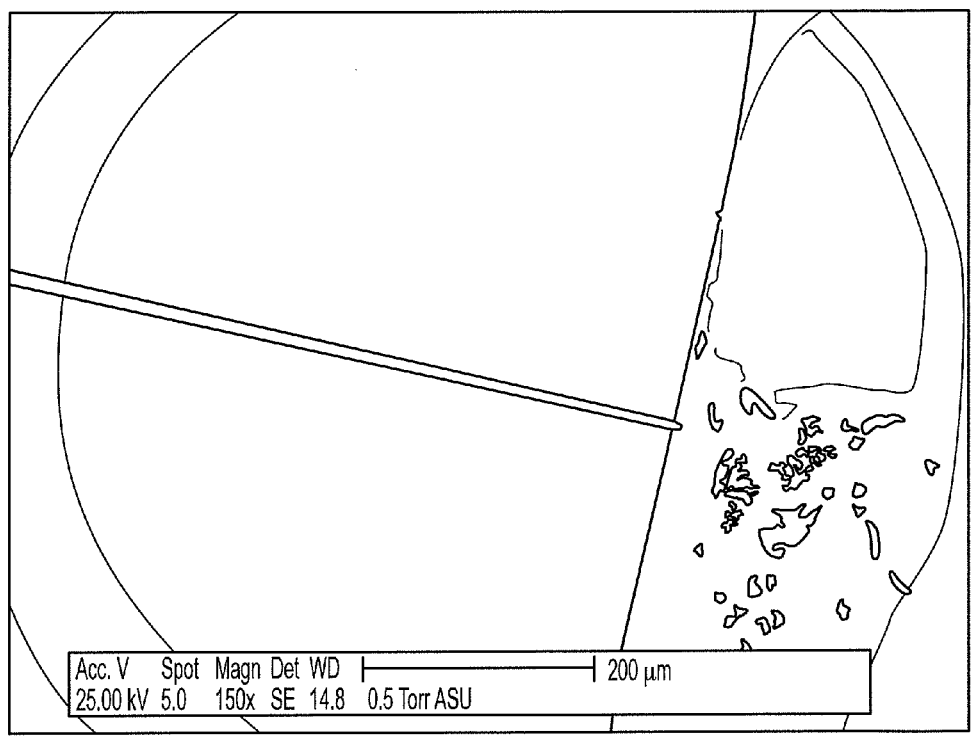
FIG. 9 is an electron microscope image of a 10 micrometer diameter liquid jet produced by an exemplary embodiment of the nozzle of the disclosure.

Being that the resolution of any form of microscopy is limited by the wavelength of the radiation employed for imaging, conventional microscopy using visible light cannot resolve features smaller than approximately one micrometer. To observe liquid jets over the range down to sub-micrometer diameter accessible using GDVN technology, it becomes necessary to employ electron microscopy. Accordingly, seminal development of electron microscopy as a tool to observe microscopic liquid jets was developed as an ancillary component of this injector development. An example is provided in FIG. 9 of an electron microscope image of a 10 micrometer diameter liquid jet.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. For example, the capillary tube 25, including the asperity 45, of the first aspect can be utilized with the housing 100 of the sixth aspect and the capillary tube 120 of the sixth aspect can be utilized with the housing 15 of the first aspect. The scope of the present invention includes any other applications in which embodiments of the above structures and fabrication methods are used. The scope of the embodiments of the present invention should be determined with reference to claims associated with these embodiments, along with the full scope of equivalents to which such claims are entitled.

We claim:

1. A nozzle assembly comprising:
    a housing, wherein a distal end of the housing defines an outlet channel;
    a capillary tube disposed within the housing, wherein a distal end of the capillary tube is tapered;
    at least one bore defined by the capillary tube, wherein the at least one bore defines a capillary outlet on a side surface of the tapered distal end; and
    an asperity defined substantially on an apex of the tapered distal end; wherein one of the following is true:
    (a) the at least one bore comprises a single bore aligned with the central axis of the capillary tube, wherein the single bore diverges from the capillary tube's central axis; or
    (b) the at least one bore is parallel to but spaced apart from the central axis of the capillary tube.

2. The nozzle assembly of claim 1, wherein the capillary tube is substantially aligned along the axis of the outlet channel.

3. The nozzle assembly of claim 1, wherein the at least one bore comprises a single bore aligned with the central axis of the capillary tube wherein the single bore diverges from capillary tube's central axis.

4. The nozzle assembly of claim 1, wherein the at least one bore is parallel to but spaced apart from the central axis of the capillary tube.

5. The nozzle assembly of claim 1, wherein the capillary tube's tapered end is substantially conical.

6. The nozzle assembly of claim 1, wherein the capillary tube's tapered end is substantially conical and beveled.

7. The nozzle assembly of claim 1, wherein the capillary tube's tapered end defines a plurality of planar flats.

8. The nozzle assembly of claim 1, wherein the capillary tube's tapered end is received in the outlet channel.

9. The nozzle assembly of claim 1, wherein the capillary tube's tapered end is positioned upstream of the outlet channel.

10. The nozzle assembly of claim 1, wherein the inner diameter of the housing is greater than the outer diameter of the capillary tube such that there is a coaxial space between the housing's inner wall and the capillary tube's external wall.

11. The nozzle assembly of claim 1, wherein the housing defines a square internal cross-section.

12. A method for manufacturing the capillary tube of claim 1:
    heating the distal end of the capillary tube;
    bending the distal end to a predetermined radius of curvature;
    cutting the distal end at a desired distance along the radius of curvature; and
    grinding a symmetrical cone onto the remaining portion of the distal end.

13. A method for manufacturing the capillary tube of claim 1:
    heating the distal end of the capillary tube until closure;
    grinding the distal end into a cone; and
    cutting at least one bevel into the cone.

14. A method for producing a liquid jet comprising:
    providing a nozzle assembly according to claim 1;
    injecting a first fluid into the proximal end of the housing; and
    injecting a second fluid into the proximal end of the capillary tube.

15. An injector comprising:
    (i) a chamber comprising a vacuum orifice and an injector orifice, wherein the chamber is adapted for use with a vacuum analysis system; and
    (ii) a nozzle assembly comprising
        (A) a housing, wherein a distal end of the housing defines an outlet channel;
        (B) a capillary tube disposed within the housing, wherein a distal end of the capillary tube is tapered;
        (C) at least one bore defined by the capillary tube, wherein the at least one bore defines a capillary outlet on a side surface of the tapered distal end; and
        (D) an asperity defined substantially on an apex of the tapered distal end, wherein the outlet channel of the nozzle outputs to the chamber and is essentially aligned with the injector orifice.

16. The injector of claim 15, wherein the chamber is adapted for use with a transmission electron microscope.

17. A nozzle assembly comprising:
    a housing, wherein the housing defines a cavity enclosed on all sides with an inlet opening at a proximal end and a de Laval Nozzle at a distal end, wherein the de Laval Nozzle defines a converging-diverging channel, and wherein a housing outlet is defined within the de Laval Nozzle at the point where the converging-diverging channel is constricted;
    a capillary tube disposed within the cavity of the housing such that there is a coaxial space maintained between the capillary tube and the housing, wherein a distal end of the capillary tube is optionally tapered;
    at least one bore defined by the capillary tube, wherein a proximal end of the at least one bore defines a capillary inlet and a distal end of the at least one bore defines a capillary outlet, wherein the capillary outlet does not extend beyond the housing outlet; and
    a first switching channel defined in the housing on a first side of a diverging section of the converging-diverging channel and a second switching channel defined in the housing on the second side of the diverging section of the converging-diverging channel, wherein the first and second switching channels are each in fluid communication with the diverging section of the converging-diverging channel;

wherein the housing further defines a first propelling channel and a second propelling channel, wherein the first and second propelling channels are each disposed substantially perpendicular to the coaxial space and are in fluid communication with the coaxial space.

18. The nozzle assembly of claim 17, wherein the housing outlet has a rectangular cross-section.

19. The nozzle assembly of claim 17, wherein the first propelling channel and the second propelling channel are on opposing sides of the housing.

20. A method for producing a liquid jet comprising:
providing a nozzle assembly according to claim 17;
injecting a first fluid into the first and the second propelling channels; and
injecting a second fluid into the capillary inlet.

21. The method for producing a liquid jet of claim 20, further comprising:
operating at subsonic flow by maintaining an upstream-to-downstream pressure ratio in the converging-diverging channel in the range of about 1.03 to about 1.89.

22. The method for producing a liquid jet of claim 20, wherein the first fluid is helium gas.

23. The method for producing a liquid jet of claim 20, further comprising:
producing a liquid jet following a boundary layer of a first side of a diverging section of a converging-diverging channel;
injecting a first puff of air into a first switching channel; and
in response to the first puff of air, switching the liquid jet to a boundary layer of a second side of the diverging section of the converging-diverging channel.

24. The method for producing a liquid jet of claim 23, further comprising:
injecting a second puff of air into a second switching channel; and
in response to the second puff of air, switching the liquid jet to the boundary layer of the first side of the diverging section of the converging-diverging channel.

25. The method for producing a liquid jet of claim 20, wherein the diverging section of the converging-diverging channel is maintained at atmospheric pressure.

26. The method for producing a liquid jet of claim 20, further comprising:
operating the diverging section of the converging-diverging channel under vacuum; and
in response to operating under vacuum, producing a liquid jet substantially centered between the first side and the second side of the diverging section of the converging-diverging channel.

27. The method for producing a liquid jet of claim 20, further comprising:
directing the liquid jet across a pulsed X-ray beam.

28. A method for manufacturing the housing of claim 17:
soft-baking photoresist that is spin-coated in a desired pattern on a silicon wafer;
exposing the photoresist to UV light through a photomask;
chemically developing the photoresist;
hard-baking the photoresist to form a negative stamp;
pouring uncured poly(dimethylsiloxane) into the negative stamp to create a layer defining a cavity and a plurality of microchannels; and
fixing the layer between a top slab and a bottom slab of poly(methyl methacrylate).

* * * * *